United States Patent [19]

Leone-Bay et al.

[11] Patent Number: 4,785,121

[45] Date of Patent: * Nov. 15, 1988

[54] PREPARATION OF HALOPHTHALIC ANHYDRIDES

[75] Inventors: Andrea Leone-Bay; Elliott Bay, both of Ridgefield, Conn.; Peter E. Timony, Valley Cottage, N.Y.

[73] Assignee: Stauffer Chemical Company, Westport, Conn.

[*] Notice: The portion of the term of this patent subsequent to Mar. 3, 2005 has been disclaimed.

[21] Appl. No.: 947,798

[22] Filed: Dec. 29, 1986

Related U.S. Application Data

[63] Continuation-in-part of Ser. No. 851,625, Apr. 14, 1986, Pat. No. 4,730,046.

[51] Int. Cl.$^4$ .................................... C07D 307/89
[52] U.S. Cl. .................................................. 549/246
[58] Field of Search ................................... 549/246

[56] References Cited

U.S. PATENT DOCUMENTS 3,956,321  5/1976  Markezich et al. ............... 549/246

OTHER PUBLICATIONS

Timokhin et al, Chemical Abstracts, vol. 101 (1984) 171369k.

Matyushecheva et al, Chemical Abstracts, vol. 80 (1974) 108490a.

Yagupol'skii et al, Chemical Abstracts, vol. 84 (1976) 135727x.

*Primary Examiner*—Richard L. Raymond
*Attorney, Agent, or Firm*—Harry A. Pacini; Hensley M. Flash

[57] ABSTRACT

A process for selectively substituting an aromatic nitro group of a nitrophthalic anhydride with a halo group which comprises contacting the nitroaromatic-containing compound with a phosphorus halide of formula:

$$R_nPX_{5-n}$$

wherein n is selected from 0, 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen. The process can take place in the presence of an arylphosphorusoxydihalide solvent or without using a solvent. The use of an arylphosphorustetrahalide and particularly phenylphosphorustetrachloride is preferred. The arylphosphorustetrahalide can be prepared in situ by contacting a solution of the corresponding arylphosphorusdihalide in an arylphosphorusoxydihalide solvent with a halogen. The process can further comprise the step of heating the reaction mixture to maintain a temperature of from about 25° C. to about 175° C. for from about 1 hour to about 24 hours.

14 Claims, No Drawings

PREPARATION OF HALOPHTHALIC ANHYDRIDES

CROSS REFERENCE TO RELATED APPLICATION

This application is a continuation-in-part of U.S. patent application Ser. No. 851,625, filed Apr. 14, 1986, now U.S. Pat. No. 4,730,046.

BACKGROUND OF THE INVENTION

1. Field of the Invention

This invention relates to a process for preparing halophthalic anhydrides and in particular to a process for selectively substituting an aromatic nitro group of a nitrophthalic anhydride with a halogen.

2. Related Information

A common problem facing organic chemists is the regio-specific halogenation of aromatic rings. One practical solution to this problem is the substitution of aromatic nitro groups by a halogen, e.g., chlorine. The Sandmeyer reaction is normally used to accomplish this conversion. The nitro group is reduced to an amine, diazotized, then reacted with copper chloride to give the corresponding chloroaromatic. A number of variations on this basic reaction are also known. Other methods of replacing an aromatic nitro group with a chlorine include irradiation in chloroform/hydrogen chloride solution, alkylative reduction by Grignard reactions quenched with sodium hypochlorite and treatment with thionyl chloride in the vapor phase.

The Sandmeyer reaction is normally the process of choice and even though this synthesis involves many steps, it offers several advantages over direct halogenation. First of all, fluorides and iodides which can seldom be prepared by direct halogenation, can be obtained from the diazonium salts. Second, where direct halogenation yields a mixture of ortho and para isomers, the ortho isomer, at least, is difficult to obtain pure. On the other hand, ortho and para isomers of the corresponding nitro compounds, from which the diazonium salts ultimately come, can often be separated by fractional distillation. For example, the boiling points of ortho- and para-bromotoluenes are only 3° C. apart (82° C. and 85° C.). The boiling points of the corresponding ortho- and para-nitrotoluenes, however, are 16° C. apart (222° C. and 238° C., respectively).

The use of phophorus halides of the formula:

$$R_nPX_{5-n}$$ 

wherein n is selected from 0, 1, 2 and 3; R is selected (when n is other than 0) from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen, and particularly the use of phenylphosphorustetrachloride (PPTC, as a reagent for organic synthesis is practically unknown when they contain aryl or substituted aryl groups. Timokhin, B. V.; Dmitriev, V. K., Dmitriev, V. I., Zh. Obshch. Khim 1984, 54, 1290, reported the reaction of cyclohexene with PPTC to give trans-1,2-dichlorocyclohexane and 3-chlorocyclohexane. Mitrasov, Y. N.; Vladyko, E. D.; Kormachev, V. V. USSR SU Nos. 1,051,097 and 1,051,096 found that treatment of aliphatic aldehydes and ketones with PPTC produced geminal dichlorides. PPTC has also been used to produce tetrazines from hydrazines, see Yagupol'skii, L. M.; Matyushecheva, G. I.; Mikhailov, V. S.; Bulygina, L. A. USSR SU No. 498,300 and Matyushecheva, G. I.; Mikhailov, V. S. Yagupol'skii, L. M., Zh. Org. Khim, 1974, 10, 124.

The halophthalic anhydrides prepared by the process of this invention, and in particular the 3-halophthalic anhydrides, are useful intermediates in the preparation of certain herbicides.

SUMMARY OF THE INVENTION

An object of this invention is to provide a process for simply preparing halophthalic anhydrides by selectively substituting the corresponding aromatic nitro group of nitrophthalic anhydride with a halo group.

A further object of this invention is the use of a phosphorus halide, and particularly an arylphosphorushalide such as PPTC, as a reagent in organic synthesis and particularly its use as a selective halogenating agent in the preparation of halophthalic anhydrides.

Other objects and advantages of the present invention are described elsewhere within this specification.

This invention is a process for selectively substituting an aromatic nitro group with a halogen which comprises contacting a compound of formula:

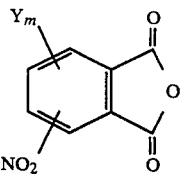

wherein m is selected from 0, 1, 2, and 3; and Y is selected independently each time it occurs from the group consisting of straight and branched chain alkyl, alkoxy, and haloalkyl; and halogen, with a phosphorus halide of formula:

$$R_nPX_{5-n}$$ 

wherein n is selected from 0, 1, 2 and 3; R is selected from the group consisting of C-6 to C-10 aryl and substituted aryl wherein the substituents are selected from the group consisting of: straight and branched chain alkyl, alkoxy and haloalkyl; halogen, sulfonate and mixtures thereof; and X is a halogen, in an amount effective to selectively denitrohalogenate said compound. In this process, a preferred phosphorus halide, e.g., an arylphosphorustetrahalide, can be prepared in situ by contacting a solution of an arylphosphorusdihalide in an arylphosphorusoxydihalide solvent with a halogen. In preferred embodiments, the nitroaromatic-containing compound is added to a solution containing the arylphosphorushalide and the resulting reaction mixture is heated to maintain a temperature of from about 25° C. to about 175° C. for from about 1 hour to about 24 hours. Phenylphosphorustetrahalide is a preferred arylphosphorustetrahalide and particularly the chloride and fluoride which are used to prepare the corresponding chloro- and fluorophthalic anhydride products.

DETAILED DESCRIPTION OF THE INVENTION

In the process of this invention, aromatic nitro groups are removed and replaced with halo groups. The major product resulting, has the aromatic nitro group replaced by a halo compound, i.e., after the nitro group is removed, thus this process is one for selectively substituting an aromatic nitro group with a halogen.

The compound containing the aromatic nitro group is a compound of the formula:

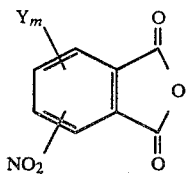

wherein m is selected from 0, 1, 2, and 3; and Y is selected independently each time it occurs from the group consisting of: straight and branched chain C-1 to C-8 alkyl, C-1 to C-6 alkoxy, and C-1 to C-8 haloalkyl; and halogens. As designated, the Y substituent can be at any available position within the aromatic nucleus and further there can be up to three separate, similar or different Y substituents. Similarly, the nitro group can be at any available position within the aromatic nucleus. In fact, as long as at least one $-NO_2$ group is on the ring, the presence of other substituents should not interfere, or at least not seriously interfere, with the selective substitution reaction. Illustrative compounds containing the aromatic nitro group include substituted phthalic anhydrides.

The phosphorus halide useful in this invention is of the formula:

wherein n, R and X are defined above. A preferred compound is an arylphosphorushalide such as an arylphosphorustetrahalide and particularly an arylphosphorustetrahalide prepared in situ by contacting an arylphosphorusdihalide in an optional arylphosphorusoxydihalide solvent with a halogen. Another preferred phosphorus halide is when n=0, e.g., phosphorus pentahalide, particularly the pentachloride.

The aryl portion of arylphosphorustetrahalide, arylphosphorusdihalide, and arylphosphorusoxydihalide (if present) can be C-6 to C-10 aryl and substituted aryl wherein the substituents can be selected from the group consisting of: straight and branched chain alkyl, alkoxy, and haloalkyl; halogen, sulfonate and mixtures thereof. The halide portions of these compounds can be any of the halogens, e.g., chlorine, bromine, iodine, and fluorine, with chlorine and fluorine being preferred.

In this process, the aromatic nitro group-containing compound is contacted with, for example, the preferred arylphosphorustetrahalide in the presence of an arylphosphorusoxydihalide solvent and in an amount effective to selectively denitrohalogenate said aromatic nitro group. The phosphorus halide can be prepared by any known method, and the preferred arylphosphorustetrahalide can preferably be prepared in sity by contacting an arylphosphorusdihalide in an optional solvent, arylphosphorusoxydihalide, with a halogen. In this preferred procedure, it is preferred to use the particular aryl halide and halogen group throughout the preparation, e.g., in the preparation of phenylphosphorustetrachloride, phenylphosphorusdichloride is contacted with chlorine gas. Phenylphosphorusoxydichloride can be used as an optional solvent. It is also preferred that the compound containing the aromatic nitro group be added to the solution containing the arylphosphorushalide.

It is believed that the mere contacting of the compound containing the aromatic nitro group and the phosphorus halide in the presence or absence of an arylphosphorusoxydihalide solvent can result in the preparation of certain quantities of the denitrohalogenated compound. However, heating the reaction mixture over a period of time can result increased yields. The reaction mixture can be heated to maintain a temperature of from about 25° C. to about 175° C., for from about 1 hour to about 24 hours, with a temperature range of from about 100° C. to about 175° C. being preferred, and maintaining a temperature of about 150° C. for about 5 hours is particularly preferred. The reactants utilized in the process of the present invention are generally employed in stoichiometric amounts, although an excess of any reagent can be used, if desired. The quantity of undesired side products, however, can be minimized by the use of approximately stoichiometric amounts of reactants. No catalyst is used or is necessary in the processes of the present invention.

The reaction times can vary over relatively wide ranges and can easily be determined by one of ordinary skill in the art. Factors affecting reaction time can include the choice of a specific reactant and a specific temperature and the choice of a solvent. Increases in temperature and reactant concentrations up to stoichiometric amounts can result in decreased reaction times. Dilute reactants usually require longer reaction time than the more concentrated reactions. The reaction is run at atmospheric pressure and it is believed that increased pressure can increase the reaction rate.

The following generalized equation represents the process of this invention:

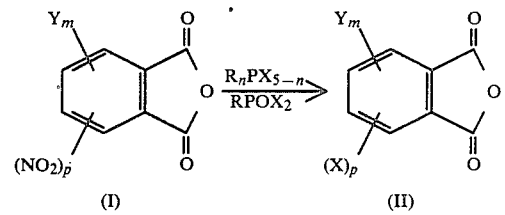

$R_nPX_{5-n}$ is the phosphorus halide and $RPOX_2$ is the arylphosphorusoxydihalide solvent which are both described above. Formula (I) represents the nitroaromatic-containing compound, herein depicted as a nitrophthalic anhydride. p is $\geq 1$ and $\leq 4$ i.e. there must be at least one nitro group and can be up to the maximum allowable four nitro groups. Y represents the optional substituent(s) on the ring and m, the number of substituents, which can be 0, 1, 2, or 3. Formula (II) represents the resulting halogenated product in which each nitro group is replaced by the halogen X.

The following experiment describes an embodiment of this invention. Other embodiments will be apparent to one of ordinary skill in the art from a consideration of this specification or practice of the invention disclosed herein. It is intended that the specification and the experiment be considered as exemplary only, with the true scope and spirit of the invention being indicated by the claims which follow the experiment.

EXPERIMENT 1

The following experiment demonstrates the use of phenylphosphorustetrachloride (PPTC) at about 150° C. to convert 3-nitrophthalic anhydride to 3-chlorophthalic anhydride.

Chlorine gas (44.6 grams, 0.63 moles) was bubbled into dichlorophenylphosphine (86 milliliters, 0.63 moles) at a sufficient rate to maintain the reaction temperature at or below 100° C. To the molten phenylphosphorustetrachloride thus prepared, 3-nitrophthalic anhydride (115 grams, 0.60 moles) was added through a solid addition funnel while maintaining a reaction temperature of about 150° C. After 12 hours at about 150° C., the reaction mixture was cooled to room temperature and the precipitated 3-chlorophthalic anhydride was removed by filtration. This material was washed with ether to yield the desired product as a pale yellow powder (87 grams, 80 weight percent) in >90 weight percent purity.

EXPERIMENT 2

Chlorine gas (363 milligrams, 5.18 millimoles) was bubbled into a solution of dichlorophenylphosphine (927 milligrams, 5.18 millimoles) in dichlorophenylphosphine oxide (10 milliliters). To this yellow solution was added 3-nitrophthalic anhydride (1 gram, 5.18 millimoles), then the reaction mixture was heated to 150° C. for 12 hours. The cooled solution was poured onto ice (20 milliliters) and neutralized with 50% aqueous sodium hydroxide. The aqueous mixture was extracted twice with 20 milliliter portions of ethyl acetate. The combined organic extracts were washed with brine, dried over magnesium sulfate and concentrated in vacuo to yield 3-chlorophthalic anhydride (780 milligrams, 83 weight percent) as a dark solid.

What is claimed is:

1. A process for selectively substituting an aromatic nitro group with a halogen which comprises: contacting a nitrophthalic anhydride with a phosphorus halide of the formula $$R_nPX_{5-n}$$

wherein n is selected from 0, 1, 2 and 3; R is selected from the group consisting of C-6 to C-10 aryl and substituted aryl wherein the substituents are selected from the group consisting of: straight and branched chain alkyl, alkoxy, and haloalkyl; halogen, sulfonate and mixtures thereof; and X is a halogen to selectively denitrohalogenate the nitrophthalic anhydride.

2. The process of claim 1 wherein the nitrophthalic anhydride is a compound of the formula:

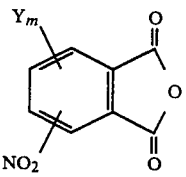

wherein m is selected from 0, 1, 2, and 3; and Y is selected independently each time it occurs from the group consisting of: straight and branched chain alkyl, alkoxy, and haloalkyl; and halogen.

3. The process of claim 2 wherein the reaction takes place in the presence of an arylphosphorusoxydihalide solvent.

4. The process of claim 3 wherein the phosphorus halide is an arylphosphorustetrahalide prepared in situ by contacting a solution of an arylphosphorusdihalide in an arylphosphorusoxydihalide solvent with a halogen gas.

5. The process of claim 4 wherein the nitrophthalic anhydride is added to the solution containing the arylphosphorustetrahalide.

6. The process of claim 5 which further comprises the step of heating the mixture resulting from the addition of the nitrophthalic anhydride.

7. The process of claim 6 wherein the resulting mixture is heated to maintain a temperature of from about 25° C. to about 175° C. for from about 1 hour to about 24 hours.

8. The process of claim 7 wherein the arylphosphorustetrahalide is phenylphosphorustetrahalide.

9. The process of claim 8 wherein the phenylphosphorustetrahalide is prepared from phenylphosphorusdihalide in phenylphosphorusoxydihalide.

10. The process of claim 9 wherein the halides are fluorides and the halogen is fluorine.

11. The process of claim 10 wherein the halides are chlorides and the halogen is chlorine.

12. The process of claim 11 wherein the nitrophthalic anhydride is 3-nitrophthalic anhydride.

13. The process of claim 1 wherein the phosphorus halide is phosphorus pentachloride.

14. The process of claim 13 wherein the nitrophthalic anhydride is added to a solution of the phosphorus pentachloride and the resulting mixture heated to maintain a temperature of from about 100° C. to about 175° C. for from about 1 hour to about 24 hours.

* * * * *